(12) United States Patent
Soldani et al.

(10) Patent No.: US 10,350,063 B2
(45) Date of Patent: Jul. 16, 2019

(54) PROCESS OF MANUFACTURING A HEART VALVE MADE OF A POLYMERIC MATERIAL AND THE HEART VALVE THEREBY OBTAINED

(71) Applicants: CONSIGLIO NAZIONALE DELLE RICERCHE, Rome (IT); HUMANITAS MIRASOLE S.P.A., Rozzano (Milan) (IT)

(72) Inventors: Giorgio Soldani, Massa (IT); Mattia Glauber, Milan (IT)

(73) Assignees: CONSIGLIO NAZIONALE DELLE RICERCHE, Rome (IT); HUMANITAS MIRASOLE S.P.A., Milan (IT)

( * ) Notice: Subject to any disclaimer, the term of this patent is extended or adjusted under 35 U.S.C. 154(b) by 22 days.

(21) Appl. No.: 15/319,362

(22) PCT Filed: Jun. 17, 2015

(86) PCT No.: PCT/IB2015/054568
§ 371 (c)(1),
(2) Date: Dec. 15, 2016

(87) PCT Pub. No.: WO2015/193824
PCT Pub. Date: Dec. 23, 2015

(65) Prior Publication Data
US 2017/0128200 A1    May 11, 2017

(30) Foreign Application Priority Data
Jun. 17, 2014    (IT) .............................. TO2014A0479

(51) Int. Cl.
*A61F 2/24*    (2006.01)
*A61L 27/18*    (2006.01)
(Continued)

(52) U.S. Cl.
CPC ............ *A61F 2/2415* (2013.01); *A61L 27/18* (2013.01); *A61L 27/507* (2013.01); *B29C 41/003* (2013.01); *B29C 41/08* (2013.01); *B29C 41/085* (2013.01); *B29C 43/003* (2013.01); *B29C 43/02* (2013.01); *B29C 43/36* (2013.01);
(Continued)

(58) Field of Classification Search
CPC ..... A61L 27/507; A61F 2/2415; B29C 41/08; B29C 41/085; B29C 41/10; B29C 43/003; B29L 2031/7534; B29L 2031/7506
See application file for complete search history.

(56) References Cited

FOREIGN PATENT DOCUMENTS

| EP | 1 431 019 B1 | 3/2007 |
|---|---|---|
| WO | WO 2014/008207 A1 | 1/2014 |

OTHER PUBLICATIONS

PCT International Search Report for PCT Counterpart Application No. PCT/IB2015/054568, 3 pp., (dated Oct. 9, 2015).
(Continued)

*Primary Examiner* — Stella K Yi
(74) *Attorney, Agent, or Firm* — Womble Bond Dickinson (US) LLP

(57) ABSTRACT

A process for the manufacture of a heart valve of polymer material which provides for the deposition of a polymer solution comprising a copolymer which is preferably a copolymer of poly(carbonato-urethane) fluoridate (F-PCU) and intracatenary polydimethylsiloxane (PDMS), a PDMS with a functional group outside the chain and a solvent onto a mould using a spray technique associated with phase inversion.

14 Claims, 4 Drawing Sheets

Figure 1A:
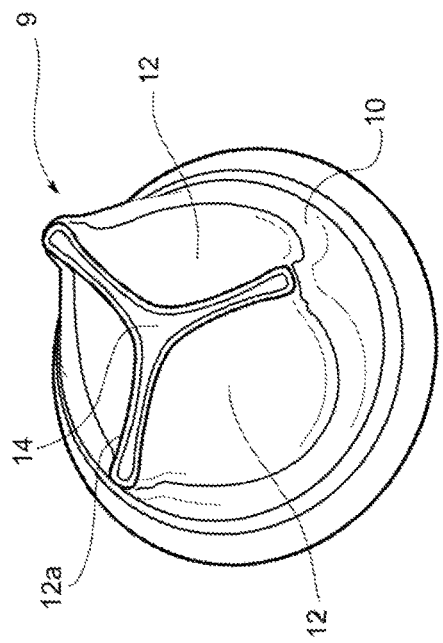
Figure 1B:
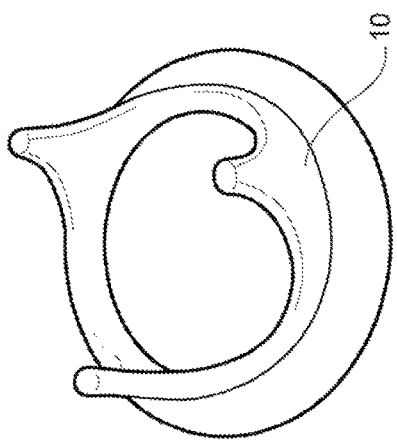

(51) Int. Cl.
  *A61L 27/50*  (2006.01)
  *B29C 41/00*  (2006.01)
  *B29C 41/08*  (2006.01)
  *B29C 43/00*  (2006.01)
  *B29C 43/02*  (2006.01)
  *B29C 43/36*  (2006.01)
  *B29C 43/52*  (2006.01)
  *B29K 69/00*  (2006.01)
  *B29K 75/00*  (2006.01)
  *B29K 83/00*  (2006.01)
  *B29L 31/00*  (2006.01)
  *C08L 83/04*  (2006.01)

(52) U.S. Cl.
  CPC ...... *B29C 43/52* (2013.01); *B29C 2043/3665* (2013.01); *B29K 2069/00* (2013.01); *B29K 2075/00* (2013.01); *B29K 2083/00* (2013.01); *B29L 2031/7506* (2013.01); *B29L 2031/7532* (2013.01)

(56) References Cited

OTHER PUBLICATIONS

PCT Written Opinion of the International Searching Authority for PCT Counterpart Application No. PCT/IB2015/054568, 4 pp., (dated Oct. 9, 2015).

Giorgio Soldani, et al., "Long Term Performance of Small-Diameter Vascular Grafts Made of a Poly(Ether)Urethane-Polydimethylsiloxane Semi-Interpenetrating Polymeric Network", Biomaterials, vol. 31, No., 9, pp. 2592-2605, (2010).

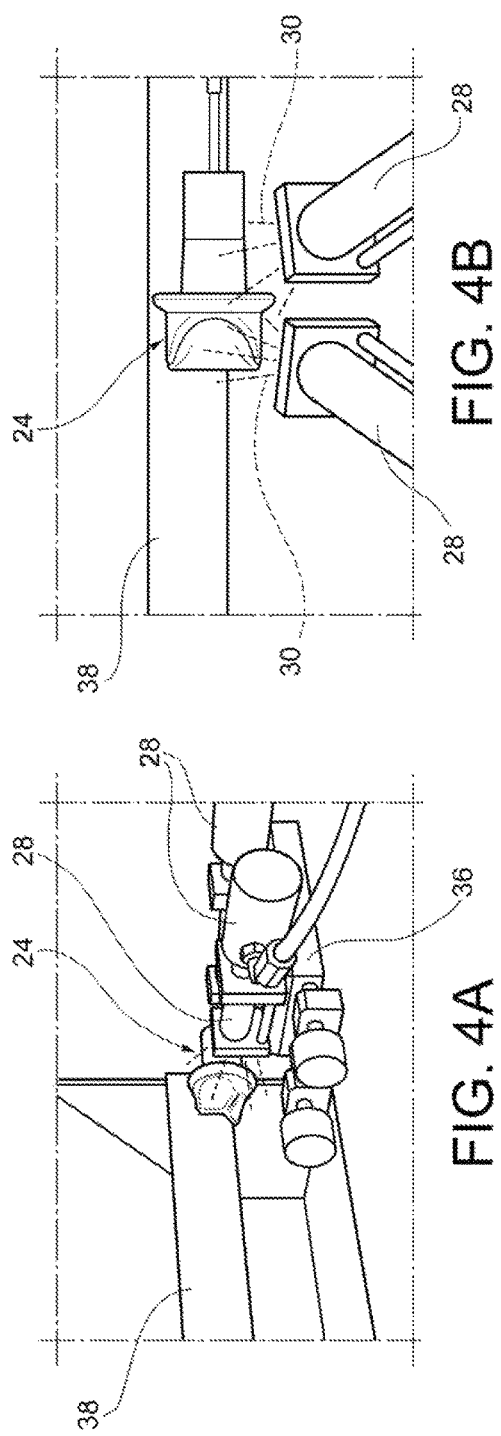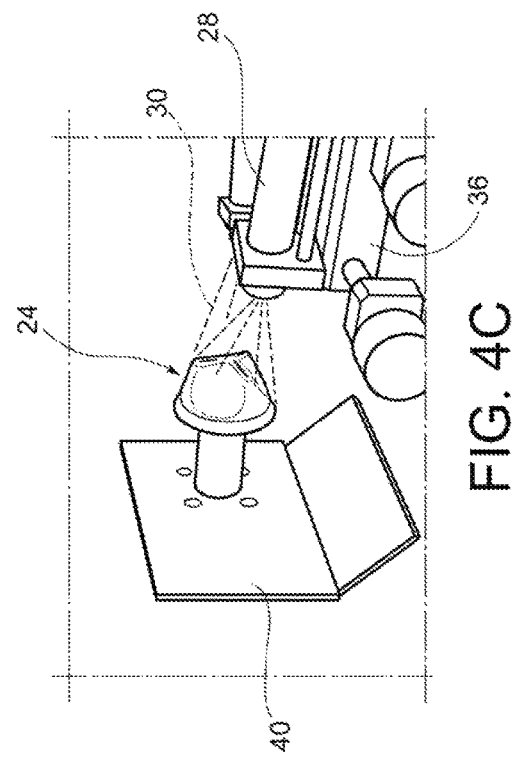

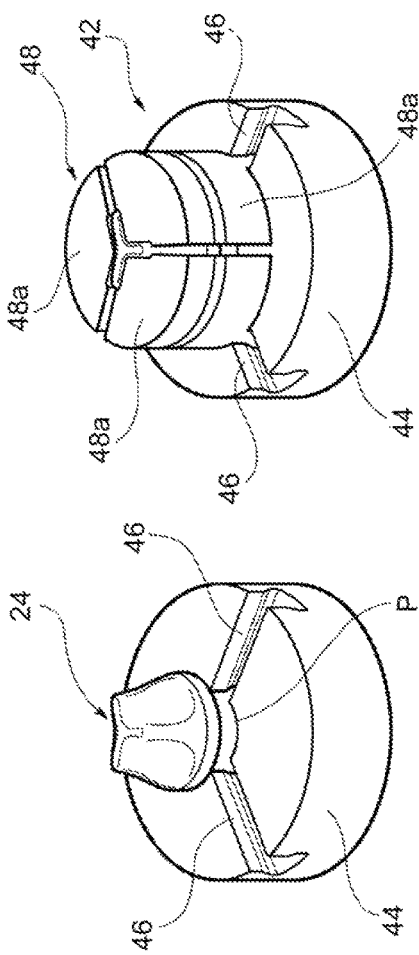
FIG. 5A
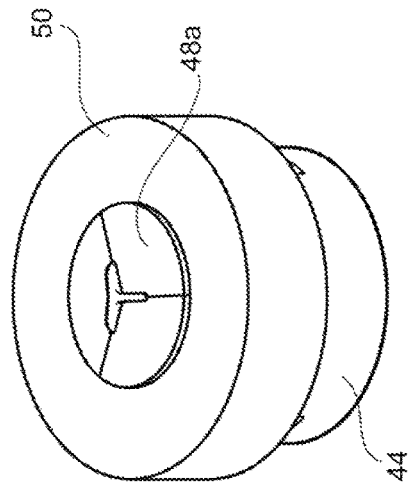
FIG. 5B
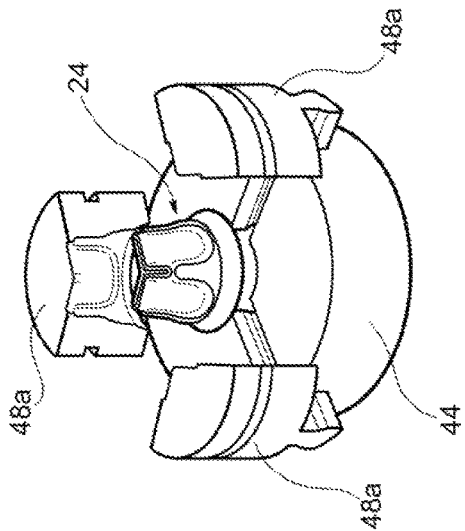
FIG. 5C
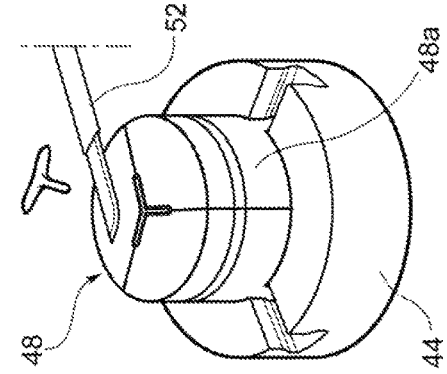
FIG. 5D
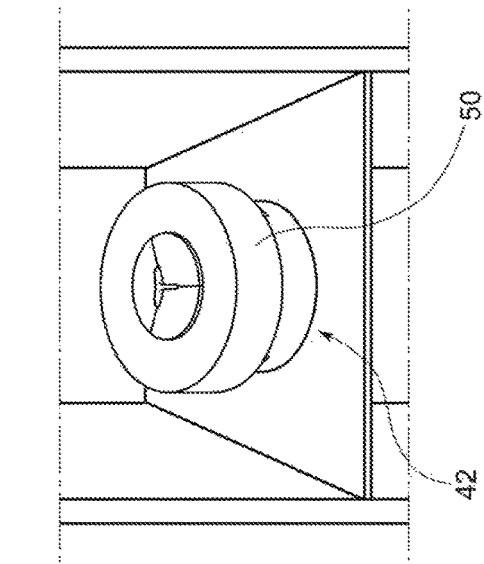
FIG. 5E
FIG. 5F ID PROCESS OF MANUFACTURING A HEART VALVE MADE OF A POLYMERIC MATERIAL AND THE HEART VALVE THEREBY OBTAINED

CROSS-REFERENCE TO RELATED APPLICATIONS

This patent application is a U.S. National Phase Application under 35 U.S.C. § 371 of International Application No. PCT/IB/2015/054568, filed Jun. 17, 2015, entitled A PROCESS OF MANUFACTURING A HEART VALVE MADE OF A POLYMERIC MATERIAL AND THE HEART VALVE THEREBY OBTAINED, which claims priority to Italian Patent Application No. TO2014A000479, filed Jun. 17, 2014.

FIELD

This invention in general relates to the sector of cardiovascular devices; in particular the invention relates to a technique for the manufacture of heart valves through the use of polymer materials.

BACKGROUND

Valve replacements are among the most widely used cardiovascular devices and the demand for them is increasing. At the present time the clinical devices available are limited to mechanical and biological valves. Long-term clinical applications of such valves are however highly problematic, given some persistent critical problems such as thrombogenicity and service life.

In fact mechanical valves have a service life and do not need repeat surgery, in that they are not subject to structural failures, but because they give rise to thromboembolic complications patients have to take anticoagulant treatments for their entire lives. Biological valve prostheses made of porcine, bovine or equine pericardium modelled and sutured onto support structures (stents) reproduce the functional biomechanical characteristics of native valves, give rise to fewer thromboembolic complications but in many cases have to be replaced 10-15 years after implant because of the occurrence of calcification problems and damage brought about by the decellularisation treatments undergone in order to reduce problems associated with immunological response.

The use of xenografts (whole valves taken from animals) and homografts (whole valves taken from cadavers) has hitherto been limited by rejection problems and very low availability.

Polymeric heart valves (hereinafter PHV) have been investigated for a long time, but their success has been impeded by very short service life due to problems with calcification, thromboembolic complications and insufficient mechanical properties of the leaflets which are the cause of malfunctioning during the stages of opening/closing. They have however found use which is limited to devices for ventricular assistance for temporary use. Use in these systems is in fact less critical because they are intended for temporary paracorporeal use (months, or at most very few years) and the patients nevertheless always receive anticoagulant therapy.

Ideally a PHV should combine the service life of mechanical valves and the haemocompatibility of biological valves, overcoming the disadvantages, mainly the thrombogenicity of mechanical valves and the poor service life of biological valves. Also new emerging therapeutic alternatives such as valve replacement by a minimally invasive percutaneous approach, which require devices capable of being collapsed and introduced within small diameter catheters, have attracted greater attention to the PHV option. Another new concept in valve replacement therapy, the tissue engineering of PHV, which uses biodegradable synthetic polymers as a scaffold, has recently increased interest in polymer materials.

Choice of material is important for the development of PHV because the material helps to provide the valve with durability and biocompatibility, so as to overcome the clinical problems associated with both mechanical and biological valves, such as thromboembolic events, undesired events due to anticoagulants and premature failure, providing improved haemodynamic functionality and service life.

Thus because a PHV is becoming a valid alternative option to valve replacement therapy the polymer selected must not only have acceptable characteristics with regard to biostability, haemocompatibility, anti-thrombogenicity, resistance to degradation and calcification, it must also have good affinity for endothelial cells.

Various synthetic polymers have been used as materials for valve leaflets, including inert synthetics such as silicone and polyolefin rubber, but these have proved to have an inadequate service life and have therefore been subsequently abandoned. Polytetrafluoroethylene (PTFE) has not had success as a material for PHV for similar reasons, in that it has given rise to a high incidence of thrombosis and calcification.

Polyurethanes (PU) are among the most popular and successful materials for biomedical applications. This class of polymer materials in fact has a number of favourable properties deriving from a two-stage microstructure consisting of rigid crystalline segments and soft elastomer segments, the ratio between which gives rise to important properties of the material such as rigidity. The rigid segments are formed by the reaction of a diisocyanate with a short chain diol or diamine ("chain extenders") typically 1,4-butanediol or ethylene diamine. The soft segments are formed by the reaction of diisocyanate with high molecular weight polyols typically within the range of 1000-2000 Daltons, such as polyethers, polyesters or polycarbonates. Their versatile characteristics, such as for example haemocompatibility and improved haemodynamic and mechanical properties, make PU useful materials for the development of cardiovascular devices.

However the main disadvantage associated with long-term applications is their low biostability, which is mainly caused by their susceptibility to degradation. The degradation of PUs is brought about by oxidation, acid hydrolysis or enzyme sequences and results in the loss of mechanical properties and eventually the creation of lacerations or cracks in the valve leaflets. The second and more serious disadvantage of PU is their tendency to calcification, which remains an appreciable obstacle to their use in long-term implants.

In order to deal with these problems efforts have been made to improve the properties of polyurethanes by modifying the soft segments, which are considered to be the most vulnerable components. Up to now three main types of PU with different soft segments, that is polyester urethanes (PEsU), polyether urethanes (PEtU) and polycarbonate urethanes (PCU) have been developed and consequently tested in biomedical applications.

The first generation of PU used in medical devices were the PEsU, but these proved unsuitable for long-term implants because of rapid hydrolysis of the soft polyester segment. PEtU on the contrary have excellent stability to hydrolysis and have therefore replaced PEsU in implantable medical devices for a couple of decades.

However, recently various studies have demonstrated that the soft segment of polyether is also susceptible to oxidative degradation and suffers environmental stress cracking under the conditions of in vivo implants.

Subsequently the third class of PUs, PCUs, have been tested and have demonstrated that they have greater stability to oxidation. In comparison with PEtUs the degree of biodegradation of PCUs has proved to be significantly lower and restricted to a thin surface layer. Replacements of the chemical structure of PUs have also been made in an attempt to increase their biostability. The, binding of biodegradation-resistant molecules to the polymer has proved an effective method for increasing the biostability of PUs. For example attempts have been made to incorporate polydimethylsiloxane (PDMS) (a molecule which imparts good thermal and oxidative stability) into the PU chain in the presence of polyhexamethylene oxide (PHMO), which is a compatibilising polyether facilitating incorporation of the non-polar PDMS macrodiol into the PU.

The idea underlying this proposed patent is the development of a new design of PHV with a geometry similar to that of a natural aortic valve (and therefore that of biological valve prostheses) which is not subject to calcification, has a long service life and a morphology such as to reduce the thromboembolic complications due to its interaction with blood flow and with cardiac and vascular tissue to a minimum.

The valve, a single body incorporated with the supporting stent, is made using a semi-interpenetrating polymer network (semi-IPN) newly synthesised on the basis of a copolymer of poly(carbonate-urethane) (PCU) and polymethylsiloxane (PDMS), cross-linked with a functionalised silicone (functional-PDMS) and capable of combining the best mechanical strength, biocompatibility and superior biostability properties of PCU with the excellent haemocompatibility and calcification-resistance properties of silicone (PDMS) as a material of manufacture.

The presence of silicone in the polyurethane chain, together with that of the cross-linking silicone forming the semi-IPN makes it possible to vary the flexibility (flex-life) and biodegradation resistance of the new valves.

As far as the design of PHV is concerned, it is well known that the structural anatomy of the natural valve plays an essential part in its operating function, providing a suitable and stable structure with specific anatomical and histological characteristics. In view of the complex anatomy of natural valves it is difficult to create structures which have the precise anatomical and functional characteristics of a native valve. However, unlike their biological counterparts, valves with synthetic leaflets can be designed in virtually any form, and this emphasises the possible importance of structural design strategies.

The process of valve manufacture is also an essential factor influencing the performance of PHV, as its effect on the durability of valves and their haemodynamic functions has been demonstrated.

Different methods of producing PHV have been investigated, such as deep coating, film-fabrication, cavity moulding and injection moulding.

Deep-coating implies the use of a specifically designed former which undergoes repeated cycles of immersion in the polymer solution and subsequent consolidation in air or in a dry air stove until the desired thickness is achieved. The concentration of the polymer solution may vary according to the polymer chosen and the stage of manufacture. Normally the deep-coating process comprises repeated immersion in a low concentration polymer solution.

The great disadvantage of this method is that it is difficult to control the thickness distribution in the leaflet precisely. Some have proposed that leaflets should be made using a single immersion in concentrated polymer solution. This would allow more accurate reproducibility and would reduce dependence on the operator to a minimum, but because of the concentrated polymer solution undesired densification of the material in different portions of the leaflets could occur.

In film-fabrication, polymer films are deposited up to a particular thickness and the leaflets are produced by cutting the film to the desired shape. The leaflets are then anchored to the valve support structure, which is manufactured separately, through the use of solvents. Finally a thermal shaping process is used to obtain the desired valve geometry. A potential disadvantage of this technique lies in the weaknesses which may be created at the point where the leaflets are anchored to the structure of the valve because of the use of polymer solvent.

Cavity moulding uses a cavity mould comprising a static portion (female) and a moving portion (male); the mould is used to manufacture the entire valve structure through introducing hot polymer, after which the sealed mould is placed in a water bath and subjected to alternating freeze/thaw cycles to form a thin polymer film.

The disadvantage of this method lies in the fact that the material has to be subjected to different thermal cycles which could affect the fatigue resistance characteristics of the valve in a manner which is difficult to foresee.

In injection moulding an injection moulding machine is used to manufacture the valve leaflets in a partly open position on a former, after which repeated baths of hot and cold water are applied in order to produce the final valve. Here again the repeated thermal cycles may affect the mechanical and biostability characteristics of the valve.

Understandably these limitations make it difficult to manufacture heart valves having high durability and haemocompatibility standards.

SUMMARY OF THE INVENTION

One object of this invention is to overcome the limitations mentioned above through a PHV which has been obtained with the help of spray-machine technology capable of producing three-dimensional structures starting from polymer solutions.

The spray-machine comprises a precision lathe capable of housing rotating formers and two spray-guns which may be positioned on a carriage capable of lateral motion so as to spray the components listed in paragraphs 1) and 2) below at the same time but separately.

1) A copolymer solution as defined in paragraph e) of appended claim 1, in which the copolymer is present in a concentration of preferably between 1 and 3% (w/v) per volume of solution. In a preferred embodiment the copolymer solution solvent is selected from the group comprising tetrahydrofuran (THF), dioxan (DX), dimethylacetamide (DMAc) and their mixtures. Particularly preferred solvents are 1:1 (v/v) mixtures of THF and DX and of THF and DMAc. In the case of PCU-PDMS copolymer the intrachain silicone is preferably present as 20% (w/w) of the total weight of the copolymer. A variable quantity, preferably from 30 to 60% (w/w), of an extrachain functionalised silicone as defined in paragraph e) of appended claim 1 is added to the above solution. The abovementioned quantity relates to the total weight of copolymer. In another preferred embodiment the PCU-PDMS copolymer (e.g. 20% intrachain) ends in fluorine atoms (fluoridate) and a variable quantity, preferably from 30 to 60% (w/w) of an extrachain functionalised silicone can also be added to this formulation.

2) A non-solvent for the polymer solution, preferably selected from water and an alcohol and their mixtures; the alcohol is for example ethyl alcohol, propyl alcohol, benzyl alcohol, etc.

In another preferred embodiment the non-solvent may contain a polysaccharide polymer in solution, for example a polysaccharide polymer comprising repeated units of maltotriose, known as pullulan, and/or gelatin. The substances dissolved in the non-solvent are incorporated into the synthetic matrix of the PHV during spray deposition and may be subsequently cross-linked to stabilise their structure within the synthetic matrix. For example, in the case of the incorporation of gelatin, once it has formed the PHV is exposed to glutaraldehyde vapours to cross-link the gelatin without direct contact with the cross-linking agent. The glutaraldehyde is then neutralised by repeated washing in glycine. In this way PHV containing gelatin and/or pullulan represent an optimum substrate for tissue engineering.

Merely by way of information and without limitation, a more detailed description of the abovementioned PCU-PDMS copolymer and its cross-linking reaction is provided below.

PCU-PDMS is a polycarbonate-urethane-silicone thermoplastic block copolymer containing silicone as a soft segment. The copolymer is synthesised by means of a continuous process through which the silicone [polydimethylsiloxane (PDMS)] is incorporated in the soft segment of the polymer together with an aliphatic polycarbonate with a terminal hydroxyl group. The rigid segment is formed of an aromatic diisocyanate [diphenylmethane-4,4'-diisocyanate (MDI)], together with a low molecular weight glycol as a chain extender. The copolymer chains, formed of blocks based on 4,4'-bis-diphenol-2,2'-propane carbonate ester, may terminate in either silicone or fluorine.

A variable quantity of from 30 to 60% of a silicone with a di-acetoxy silyl termination (functional tetra-acetoxy) which is capable of reacting with other molecules of the same species in the presence of water forming PDMS cross-linking which is semi-interpenetrating with the PCU molecule is added to the above material with either a silicone or fluorine (fluoridate) terminal group.

Cross-linking of the PDMS with extrachain functional groups initiated by the non-solvent (for example water) during the spray deposition process is completed by standing a valve device in water heated to approximately 60° C. while the solvent is removed, or by placing it in a heated stove and subsequently standing it in water heated to approximately 60° C.

The spray-guns focus their jets at a specific point on the former. A spray machine having similar characteristics is described in EP 1 431 019.

Intersection of the flows induces rapid precipitation of the polymer onto the former (phase inversion), faithfully reproducing its geometry and making it possible to generate a three-dimensional "non-woven" filamentous structure which can have different porosities, properties and morphological characteristics depending upon the adjustment of the manufacturing variables.

PHV obtained using this technology can be effectively stored even in dehydrated form to be rehydrated at the time of use, and in hydrated form, keeping them immersed in aqueous solution.

The valve obtained by the process according to this invention is characterised by the fact that it comprises a single piece and has no discontinuities, and therefore results in very good haemocompatibility, as well as not requiring chronic anticoagulant treatment, and a reliability and service life such as to allow it to be implanted into a human being or animal as a permanent valve prosthesis.

The above and other objects and advantages are accomplished according to one aspect of the invention by a system having the characteristics defined in claim 1. Preferred embodiments of the invention are defined in the dependent claims.

BRIEF DESCRIPTION OF THE DRAWINGS

The functional and structural characteristics of some preferred embodiments of a technique for the manufacture of polymeric heart valves according to the invention will now be described. Reference will be made to the appended drawings, in which:

FIGS. 1A and 1B are diagrammatical perspective views of a polymeric heart valve obtained by an embodiment of the process according to the invention, in the open and closed configurations;

FIGS. 2A and 2B are diagrammatical perspective views of a mould and support for the manufacture of the valve illustrated in FIGS. 1A and 1B;

FIG. 3 shows a partial functional diagram of equipment for manufacturing the polymeric heart valve in the preceding figures according to an embodiment of the process according to the invention;

FIGS. 4A, 4B and 4C are diagrammatical perspective views of details of the machine in FIG. 3 during particular stages in the process according to the invention;

Figures from 5A to 5F are diagrammatical perspective views of some stages in the process according to one embodiment of the invention.

DETAILED DESCRIPTION

Before explaining the plurality of embodiments of the invention in detail, it must be pointed out that in its application the invention is not limited to the construction details and configurations of components described in the description below or illustrated in the drawings. The invention is capable of adopting other embodiments and being implemented or carried out in practice in different ways. It should also be understood that the phraseology and terminology are of a descriptive nature and should not be understood as being limiting. The use of "includes" and "comprises" and their variations are to be understood as including the items listed below and their equivalents, as well as additional elements and their equivalents.

Initially with reference to FIG. 1, a polymeric heart valve 9 comprises an annular support 10 and a plurality of flexible leaflets or leaflets 12, shaped so as to form a Y-shaped through passage 14. This passage 14 dilates and closes as the upper edges 12*a* of leaflets 12 move apart or together in such a way as to allow rather than inhibit the blood flow passing through valve 9.

Annular support 10 (which can be seen in FIG. 2B), generally comprises a lower ring 10*a* on which there is mounted a wavy crown formed of three rounded projections 10*b*, joined together at the bottom by arched sections 10*c*. From tests made to prevent tearing of valve leaflets 12, rounded projections 10*b* must have a height of between 13 and 3 mm measured from the apex of projection 10*b* to the base of the crown (or lower ring 10*a*). If projections 10*b* are of shorter height the crown is more level, and as a consequence there is a smaller concentration of stresses loading the joining lines between the crown and leaflets.

The overall architecture of the valve, which is in itself known, will not be further described.

Figure 2A:
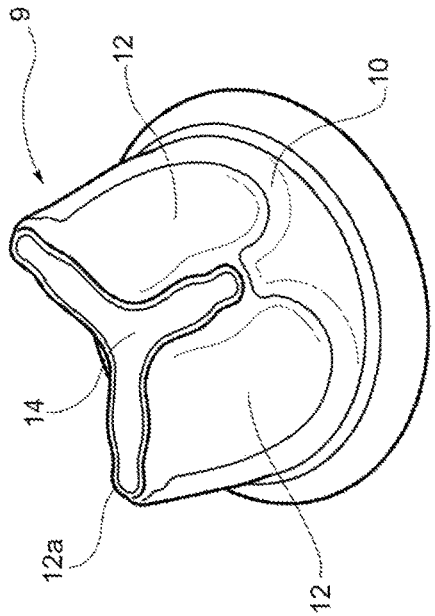
Figure 2B:
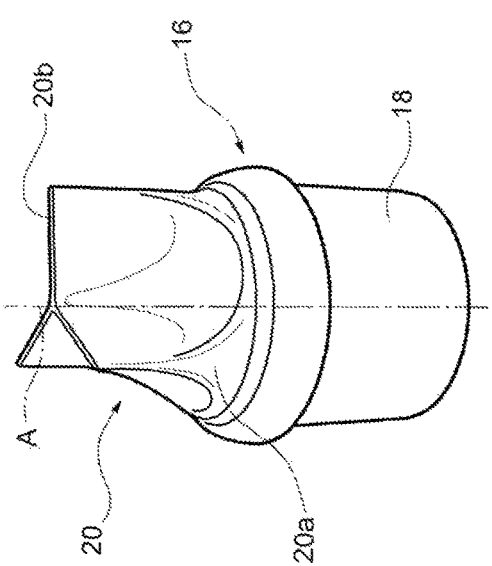

In order to manufacture the valve from the preselected polymer material, the characteristics and composition of which have been described previously, a mould 16 (which may be seen in FIG. 2A) provided with a shaft 18 and shaped in such a way that the polymer forms the profile of valve 9 when it becomes attached to outer surface 20 of mould 16 is prepared. Mould 16, which in the example illustrated has a shape which can be inscribed in a gently tapering cylinder or frustoconical shape has a lateral surface 20*a* which extends along a longitudinal axis A of the mould and a front surface 20*b* which is projected along axis A in the plane of confluence of the leaflets or the plane which contains the Y-shaped line where the flexible leaflets of valve 9 are joined at the top. Annular support 10, to which the base of leaflets 12 will adhere along their lower arch, is then made of one piece with mould 16.

Figure 3:
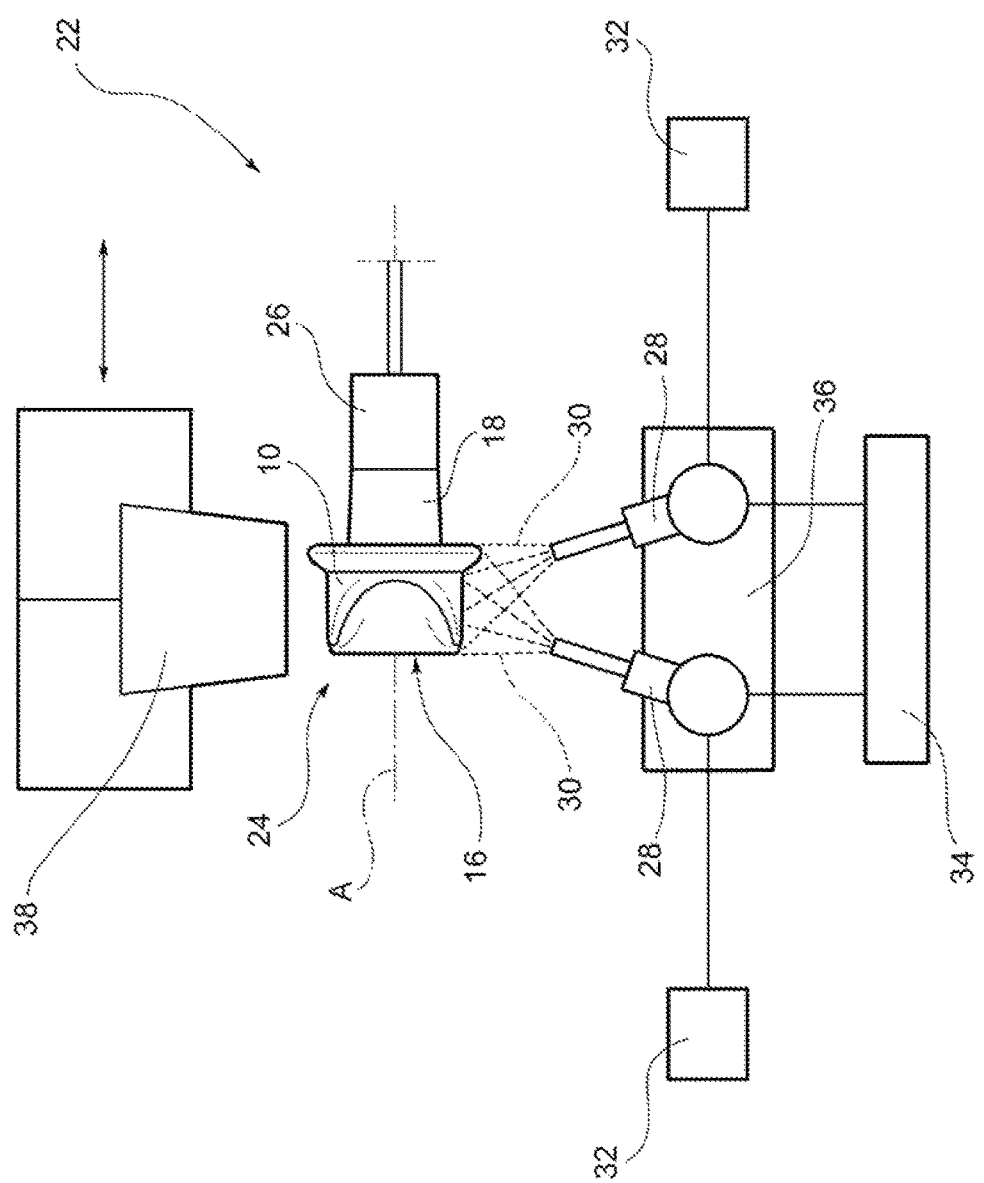

FIG. 3 shows the circuit diagram for a portion of a spray machine 22 for the manufacture of heart valve 9. In a first stage of the process of valve manufacture according to the invention the mould and the support are joined together in one piece, the assembly forming a former 24, and caused to rotate about longitudinal axis A, for example by attaching shaft 18 of the former to a rotating tailpiece 26 located on machine 22.

A pair of sprays 28 is orientated in such a way as to direct two spray jets 30 generated by respective nozzles onto former 24 along a direction which is substantially transverse with respect to longitudinal axis A.

In all this description and the claims the terms and expressions indicating positions and orientations, such as "longitudinal", "transverse", "vertical", or "horizontal" relate to longitudinal axis A.

Each spray 28 is fed separately through corresponding tanks 32 in such a way as to produce two independent jets 30 which intersect close to former 24, giving rise to the phenomenon known as phase inversion. Optionally the sprays can be orientated, including independently, in such a way as to cause jets 30 to converge or diverge, so as to concentrate or dilute the polymer in the intersection zone.

One spray respectively will be fed with a polymer solution, while the other will generate a flow of non-solvent which by intersecting the jet of polymer solution will give rise to precipitation of the polymer on the former. Deposition of the polymer on former 24 will give rise to a three-dimensional filamentous structure of the "non-woven" type.

Qualities of the filamentous structure such as porosity, thickness and other morphological characteristics can be adjusted by adjusting the strength of the jets by means of a central control unit 34, altering the orientation of the jets and/or their position with respect to the longitudinal axis of former 24. According to one embodiment of the invention sprays 28 are positioned on a powered carriage 36 which can move laterally along a direction parallel to longitudinal axis A of the former in such a way as to vary the point of incidence of the jets along the length of longitudinal axis A.

In an embodiment which is not illustrated the sprays may be attached to the powered carriage by means of spherical connectors which make it possible to orientate the axis of the jets in such a way that they are also incident on the former in directions which are not perpendicular with respect to axis A.

Preferably a suction head 38 is located on one side opposite the nozzles with respect to longitudinal axis A of the former in such a way as to remove substances which do not precipitate on the former. Head 38 may move longitudinally in synchrony with the similar movement of the nozzles.

Conveniently, once processing with the jets orientated to generate deposition of the polymer on the former in a direction substantially transverse with respect to longitudinal axis A has been completed, or when the polymer deposited on lateral surface 20*a* of the mould has achieved the desired uniformity and thickness, the former is caused to rotate 90° towards the sprays so that the jets produced by the nozzles are incident on front surface 20*b* of the mould.

According to an embodiment which is not illustrated it is possible to arrange machine 22 in such a way that instead of causing the former to rotate (for example by removing shaft 18 from rotating tailpiece 26 and securing it to a supporting plate 40, as may be seen in FIG. 4C), the sprays can be rotated through 90° in such a way as to locate the jets frontally with respect to the former, or have the effect that the jets intersect along a direction parallel to or coincident with longitudinal axis A. Similar positioning of the sprays may for example be achieved by causing the carriage to move along a curved guide track which intersects longitudinal axis A.

According to a further embodiment of the invention (not illustrated), after a preliminary layer of polymer material has been deposited onto former 24 (that is interrupting the stage of depositing polymer onto lateral surface 20*a* of the former before the said polymer has achieved the desired final thickness), it is possible to cover this material with a thin reinforcing mesh, in the form of a caul, preferably made using threads of elastomer material as an interconnected warp, whose diameter may vary between 10 and 100 microns and the size of the mesh opening of which may vary between 0.2 and 2.0 mm. The elastomer threads may be made of different resilient materials, for example: urethane polyester (PEsU), urethane polyether (PEtU), urea polyurethane (PUR) or those based on urethane polycarbonate (PCU) and urethane polycarbonate (PCU)—polydimethylsiloxane (PDMS) copolymers. Possibly, after deposition of the polymer onto lateral surface 20*a* of the former has been interrupted (before the said polymer has achieved the desired final thickness), a similar preliminary layer of material may also be deposited on front surface 20*b* of the former in order to then insert the reinforcing mesh.

Once inserted the elastomer mesh matches the geometry of the former and becomes incorporated with the material previously deposited upon it. After this stage deposition of polymer on former 24 is continued until the thin mesh is completely incorporated in the thickness of the valve leaflets, and the desired thickness and uniformity of the material coating the former is achieved. The presence of the elastomer mesh within the valve leaflets is intended to increase their mechanical resistance to fatigue, preventing possible failure and tearing of the leaflets.

Once this cycle of depositing polymer onto the former has been completed, any excess solvent is removed, for example by immersion in distilled water heated to approximately 60° C.

The former is then housed in an outer mould 42, which may be seen in FIG. 5B. Preferably outer mould 42 comprises a body 44 on which Y-shaped grooves 46 are conveniently excavated, flowing towards a central point P in which the shaft of the former is inserted.

A modular outer mould 48 comprises separate portions or modules 48a which can slide within grooves 46 in body 44 in such a way as to close onto the former, adhering thereto so as to impart the desired curvature on leaflets 12. In fact said modules 48a have an internal surface whose shape imparts the preselected profile of the leaflets onto the non-woven tissue deposited on the former. In the case illustrated here, because the leaflets of valve 9 are three in number, matrix 48 is subdivided into the same number of modules 48a.

Mould modules 48a are then pressed radially against former 24 so as to impart the shape of the valve as designed onto the precipitated polymer; the pressure of the outer mould onto the former gives rise to a partial escape of polymer material through the gaps between the modules, due to compression of the material within the outer mould. This compressive action is maintained during the subsequent stages of the process until the mould is reopened.

In order to do this, the mould, once the modules have been pressed against the former so as to form an assembly of cylindrical shape, is held in the closed position by means for example of a metal ring 50 in such a way that subsequent stages of the process do not allow the pressed polymer material to expand and the modules of the mould to move apart.

The assembly of former, outer mould and metal containing ring is placed in water heated to approximately 60° C. or in a heated stove and subsequently in water heated to approximately 60° C. for the time required for complete cross-linking of the material and removal of the solvent. The force of the outer mould also favours compaction of the deposited polymer composite structure/reinforcing mesh of elastomer thread, where the stage of covering the former with the said reinforcing mesh is provided.

Once the heat cycle has been completed and the polymer materials have become consolidated the aforesaid assembly is removed from the heated bath or stove and subsequent heated bath. The excess material leaving mould 48 through the compressive force exerted by the outer mould onto the former is removed by suitable means (for example a knife 52 as illustrated in FIG. 5E or laser cutting).

Finally modules 48a of the outer mould are separated and the mould opened in this way allows the former to be extracted, after which mould 16 is separated from the heart valve finally formed by the deposition of polymer onto the outer part of annular support 10 (lower ring 10a surmounted by a wavy crown formed of three rounded projections 10b).

The advantage accomplished is that of obtaining a heart valve of polymer material made in such a way that the polymer material is dosed in an optimal way, at the same time ensuring maximum flexibility and accuracy when defining the valve's structural parameters.

Different aspects and embodiments of a technique for the manufacture of polymeric heart valves according to the invention have been described. It is intended that each embodiment should be capable of being combined with any other embodiment. The invention is also not limited to the embodiments described, but may be varied within the scope defined by the appended claims.

What is claimed is:

1. A process for manufacturing a heart valve made of a polymer material, comprising:
    a) providing a mould shaped so as to replicate a profile to be conferred upon a valve;
    b) inserting an annular support onto the mould, so that the mould and support assembly forms a former;
    c) providing an apparatus for depositing a polymer material onto the former, which comprises a pair of spray guns arranged transversely with respect to a longitudinal axis of the former;
    d) rotating the former about the longitudinal axis;
    e) feeding one spray gun separately with a polymer solution comprising:
        (i) a copolymer containing an intrachain silicone [polydimethylsiloxane (PDMS)] and a polymer selected from the group consisting of a fluorinated poly (carbonate-urethane) (F-PCU), a polycarbonate urethane (PCU), a polyether urethane (PEtU), a polyurethane urea (PUR), a polycaprolactone (PCL);
        (ii) an extrachain functionalized PDMS, terminating in two diacetoxy silyl groups, which is able to cross-link itself thereby forming a semi-interpenetrating polymer network(semi-IPN) with the copolymer (i); and
        (iii) a solvent;
        and the other spray gun with a non-solvent for the polymer solution, said non-solvent being selected from the group comprising water, alcohols and mixtures thereof,
        so as to generate two jets that intersect along a direction substantially transverse to said longitudinal axis;
    f) keeping the jets focused on one or more sections of a lateral surface of the former until desired parameters of polymer thickness and distribution on the lateral surface of the former are satisfied;
    g) directing the jets to impact against a front surface of the former;
    h) keeping the jets focused frontally against the former, until the desired parameters of polymer thickness and distribution over the entire front surface of the former are satisfied;
    i) eliminating residual solvent traces;
    j) inserting the former into an outer mould comprising outer mould modules;
    k) radially compressing the former within the modules, continuing to exercise the compression force during subsequent process operations;
    l) heating the outer mould containing the former until cross-linking of the polymer material deposited on the former is complete;
    m) removing excess material from a resulting polymeric valve;
    n) opening the mould, removing the radial compression force of the outer mould against the former, and extracting the former from the outer mould; and
    o) removing the polymeric valve, including a support ring, from the mould.

2. The process according to claim 1, wherein the copolymer (i) contains a fluorinated poly (carbonate-urethane) (F-PCU) and an intrachain silicone [polydimethylsiloxane (PDMS)], and the copolymer is present in the polymer solution at a concentration ranging from 1% to 3% w/v per volume of the solution.

3. The process according to claim 2, wherein the intrachain silicone (PDMS) is present as about 20% (w/w) of the total weight of the co-polymer.

4. The process according to claim 1, wherein the solvent is selected from the group comprising tetrahydrofuran, dioxane, dimethylacetamide and mixtures thereof.

5. The process according to claim 4, wherein the solvent is a 1:1 mixture (v/v) of tetrahydrofuran and dioxane or tetrahydrofuran and dimethylacetamide.

6. The process according to claim 1, wherein the extrachain functionalized PDMS terminating in two diacetoxy silyl groups is present in the polymer solution at a concentration varying between 30% and 60% (w/w) of the total weight of polymer material.

7. The process according to claim 1, wherein the non-solvent is selected from the group comprising water, ethyl alcohol, propyl alcohol, benzyl alcohol and mixtures thereof.

8. The process according to claim 7, wherein the non-solvent contains pullulan and/or gelatin in solution.

9. The process according to claim 1, wherein during operations (f) and/or (g) and/or (h) the jets are made to converge or diverge with respect to directions imposed on the jets in previous operation/operations, to adjust a polymer density in the area in which the aforesaid jets intersect.

10. The process according to claim 1, wherein operation (f) is carried out by moving the spray guns laterally along a direction parallel to the longitudinal axis.

11. The process according to claim 1, wherein operation (g) is carried out while keeping the jets oriented as in operation (f), and rotating the former so that the longitudinal axis is arranged parallel to said direction of the jets.

12. The process according to claim 1, wherein between operation (f) and operation (g), or between operation (h) and operation (i), there is interposed the operation of coating the former with a reinforcing resilient mesh, said operation being followed respectively by repeating operation (f) or by repeating operations (f) to (h), until desired parameters of polymer thickness and distribution on the former are satisfied.

13. The process according to claim 1, wherein at operation (b) a support ring comprises a wavy crown formed by three rounded projections, mutually radiused at a bottom by arched sections, rounded projections having a height of between 13 mm and 3 mm measured from a top of the projection to a lower ring.

14. A polymeric heart valve, wherein it is obtainable by a process for manufacturing a heart valve made of a polymer material, and in that the polymeric heart valve has a single-piece polymer structure without discontinuities, wherein the process comprises:
   a) providing a mould shaped so as to replicate a profile to be conferred upon a valve;
   b) inserting an annular support onto the mould, so that the mould and support assembly forms a former;
   c) providing an apparatus for depositing a polymer material onto the former, which comprises a pair of spray guns arranged transversely with respect to a longitudinal axis of the former;
   d) rotating the former about the longitudinal axis;
   e) feeding one spray gun separately with a polymer solution comprising:
      (i) a copolymer containing an intrachain silicone [polydimethylsiloxane (PDMS)] and a polymer selected from the group consisting of a fluorinated poly (carbonate-urethane) (F-PCU), a polycarbonate urethane (PCU), a polyether urethane (PEtU), a polyurethane urea (PUR), a polycaprolactone (PCL);
      (ii) an extrachain functionalized PDMS, terminating in two diacetoxy silyl groups, which is able to cross-link itself thereby forming a semi-interpenetrating polymer network(semi-IPN) with the copolymer (i); and
      (iii) a solvent;
      and the other spray gun with a non-solvent for the polymer solution, said non-solvent being selected from the group comprising water, alcohols and mixtures thereof,
   so as to generate two jets that intersect along a direction substantially transverse to said longitudinal axis;
   f) keeping the jets focused on one or more sections of the lateral surface of the former until the desired parameters of polymer thickness and distribution on a lateral surface of the former are satisfied;
   g) directing the jets to impact against a front surface of the former;
   h) keeping the jets focused frontally against the former, until desired parameters of polymer thickness and distribution over the entire front surface of the former are satisfied;
   i) eliminating residual solvent traces;
   j) inserting the former into an outer mould comprising outer mould modules;
   k) radially compressing the former within the modules, continuing to exercise the compression force during subsequent process operations;
   l) heating the outer mould containing the former until cross-linking of the polymer material deposited on the former is complete;
   m) removing excess material from a resulting polymeric valve;
   n) opening the mould, removing the radial compression force of the outer mould against the former, and extracting the former from the outer mould; and
   o) removing the polymeric valve, including a support ring, from the mould.

* * * * *